United States Patent [19]

Arhancet

[11] Patent Number: 5,396,005
[45] Date of Patent: Mar. 7, 1995

[54] COMPOSITIONS AND METHODS FOR INHIBITING POLYMERIZATION OF ETHLENICALLY UNSATURATED MONOMERS

[75] Inventor: Graciela B. Arhancet, Katy, Tex.

[73] Assignee: Betz Laboratories, Inc., Trevose, Pa.

[21] Appl. No.: 183,547

[22] Filed: Jan. 19, 1994

[51] Int. Cl.⁶ ................................................ C07C 7/20
[52] U.S. Cl. ................................ 585/5; 585/2; 585/3; 585/4
[58] Field of Search ................................ 585/2, 3, 4, 5

[56] References Cited

U.S. PATENT DOCUMENTS 4,929,778  5/1990  Roling ................................. 585/3

FOREIGN PATENT DOCUMENTS 67135  10/1979  Romania .
1098200  7/1982  U.S.S.R. .

*Primary Examiner*—Asok Pal
*Attorney, Agent, or Firm*—Alexander D. Ricci; Philip H. Von Neida

[57] ABSTRACT

Disclosed are compositions and methods for inhibiting polymerization of ethylenically unsaturated monomers. The compositions comprise a methoxyphenol compound selected from the group consisting eugenol and 2-tert-butyl-4-hydroxyanisole and a phenylenediamine compound. The methods comprise adding from about 1 to about 10,000 parts per million to the ethylenically unsaturated monomer during processing.

12 Claims, No Drawings

COMPOSITIONS AND METHODS FOR INHIBITING POLYMERIZATION OF ETHLENICALLY UNSATURATED MONOMERS

FIELD OF THE INVENTION

The present invention pertains to compositions and methods for inhibiting the undesired polymerization of ethylenically unsaturated hydrocarbons during processing.

BACKGROUND OF THE INVENTION

It is well known that ethylenically unsaturated compounds readily polymerize when heated and that the polymerization rate increases with increasing temperature. A significant problem occurs during processing of hydrocarbon streams containing ethylenically unsaturated compounds, in particular butadiene, where thermal polymerization results in equipment fouling or agglomeration during the many stages of handling, purification, and storage.

Common industrial methods for producing ethylenically unsaturated monomers include a variety of purification processes, including distillation to remove impurities. Unfortunately, purification operations carried out at elevated temperatures result in an increased rate of undesired polymerization. Polymerization, such as thermal polymerization, during the monomer purification process, results not only in loss of desired monomer end-product, but also in loss of production efficiency caused by polymer formation or agglomeration on process equipment. In heat requiring operations, such agglomeration adversely affects heat transfer efficiency.

SUMMARY OF THE INVENTION

Disclosed are methods for inhibiting the polymerization of ethylenically unsaturated monomers such as butadiene and isoprene during their processing.

DESCRIPTION OF THE RELATED ART

Romanian patent 67,135 teaches the use of combinations of phenylenediamine and alkylphenols, 2,4-dimethyl-6-tert-butylphenol and 4-methyl-2,6-di-tert-butylphenol (BHT), to inhibit polymerization in pyrolysis gasoline.

Russian patent 1,098,200 teaches the use of mixtures of aromatic amines and hindered phenols to inhibit the polymerization of isoprene in synthetic rubber production. U.S. Pat. No. 4,929,778 teaches the use of a phenylenediamine and a hindered phenol for the inhibition of styrene polymerization.

DETAILED DESCRIPTION OF THE INVENTION

The present invention relates to methods and compositions for inhibiting the polymerization of ethylenically unsaturated monomers comprising adding to said monomers during processing a combination comprising a methoxyphenol compound and a phenylenediamine compound.

The ethylenically unsaturated monomers are characterized as polymerizable ethylenically unsaturated hydrocarbons and include olephins such as alpha olefins containing 2 to 20 carbon atoms and preferably 2 to 8 carbon atoms and conjugated di-olefins, preferably those containing 4 to 6 carbon atoms such as isoprene and butadiene.

The preferred methoxyphenol compounds are eugenol and 2-tert-butyl-4-hydroxyanisole.

The phenylenediamine component of the inhibitor mixtures of this invention include phenylenediamine and derivatives thereof having at least one N-H group. It is thought that o-phenylenediamine or derivatives thereof having at least one N-H group are suitable in accordance with the instant invention. However, the preferred phenylenediamine is p-phenylenediamine having the formula

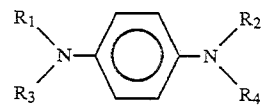

wherein $R_1$, $R_2$, $R_3$ and $R_4$ are the same or different and are hydrogen, alkyl, aryl, alkaryl, aralkyl groups with the proviso that at least one of $R_1$, $R_2$, $R_3$ or $R_4$ is hydrogen, more preferably the alkyl, aryl alkaryl, and aralkyl groups have one to about twenty carbon atoms. The alkyl, aryl, alkaryl, and aralkyl groups may be straight or branched-chain groups.

Exemplary p-phenylenediamines include p-phenylenediamine wherein $R_1$, $R_2$, $R_3$ and $R_4$ are hydrogen; N-phenyl-N'-alkyl p-phenylenediamines such as, N-phenyl-N'-methyl-p-phenylenediamine, N-phenyl-N'-ethyl-p-phenylenediamine, N-phenyl-N'-propyl-p-phenylenediamine, N-phenyl-N'-isopropyl-p-phenylenediamine, N-phenyl-N'-n-butyl-p-phenylenediamine, N-phenyl-N'-isobutyl-p-phenylenediamine, N-phenyl-N'-sec-butyl-p-phenylenediamine, N-phenyl-N'-tert-butyl-p-phenylenediamine, N-phenyl-N'-n-pentyl-p-phenylenediamine, N-phenyl-N'-n-hexyl-p-phenylenediamine, N-phenyl-N'-(1-methylhexyl)-p-phenylenediamine, N-phenyl-N'-(1,3-dimethylbutyl)-p-phenylenediamine, N-phenyl-N'-(1,4-dimethylpentyl)-p-phenylenediamine; N-phenyl-N',N'-dialkyl-p-phenylene diamines such as N-phenyl-N'-,N'dimethyl-p-phenylenediamine, N-phenyl-N',N'-diethyl-p-phenylenediamine, N-phenyl-N',N'-di-n-butyl-p-phenylenediamine, N-phenyl -N',N'-di-sec-butyl-p-phenylenediamine, N-phenyl-N'-methyl-N'-ethyl-p-phenylenediamine; N,N-dialkyl-p-phenylenediamines such as N,N-dimethyl-p-phenylene diamine and N,N'-diethyl-p-phenylenediamine; N,N'-dialkyl-p-phenylenediamines such as N,N'-di-isopropyl-p-phenylenediamine; N,N'-di-isobutyl-p-phenylenediamine; N,N'-diaryl-phenylenediamines such as N,N'diphenyl-p-phenylenediamine; N,N,N'-trialkyl-p-phenylenediamines such as N,N,N'-trimethyl-p-phenylenediamine, N,N,N'-triethyl-p-phenylenediamine. Preferably, the p-phenylenediamine is selected from the group consisting of N,N'-di-isobutyl-p-phenylenediamine, N,N'-bis-di-sec-butyl-p-phenylenediamine, N-phenyl-N'-(1,3-dimethylbutyl)-p-phenylenediamine and N-phenyl-N'-(1,4-dimethylpentyl)-p-phenylenediamine.

The total amount of methoxyphenol and phenylenediamine compound used in the methods of the present invention is that amount which is sufficient to effect inhibition of polymerization and will, of course, vary according to the processing conditions. At higher processing temperatures, larger amounts of the polymerization inhibiting treatment are generally required.

Preferably, the total amount of the treatment of methoxyphenol and phenylenediamine compound is from about 1 part per million to about 10,000 parts per million parts combined treatment based on the weight of the monomer. Most preferably, the total amount of the combination is from about 5 parts per million to about 1000 parts per million based on the weight of the monomer.

The methods of the present invention can control the fouling of processing equipment, such as the equipment used in processing of the monomer, which is due to or caused by the polymerization of the monomer. This factor is especially important in monomer purification procedures where the obvious goal of the process is to provide high level monomer purity.

The composition may be added as either a dispersion or a solution using a suitable liquid carrier dispersing medium or solvent which is compatible with the monomer. Preferably, a solution is provided and the solvent is an organic solvent such as xylene (a commercial mixture of o, m and p isomers), or heavy aromatic naphtha.

The preferred inventive embodiment employs eugenol with UOP-5 ® or Naugard ® I-3. UOP-5 ® is N,N'-bis-di-sec-butyl-p-phenylenediamine. Naugard ®I-3 is N-phenyl-N'-(1,4-dimethylpentyl)-p-phenylenediamine.

EXAMPLES

The invention will now be further described with reference to a number of specific examples which are to be regarded solely as illustrative, and not as restricting the scope of the invention.

The effectiveness of the inhibitor composition was tested under the heat induced gum test. Isoprene was chosen as the diolefin in the testing because of its ease of handling over butadiene. Freshly distilled uninhibited isoprene (10 ml) was dissolved in 40 ml of heptane, the appropriate treatment was added and the solution was placed in a test bomb. In one mode of experiments, the bomb was pressurized with 100 psig of nitrogen and heated at 100° C. for 4 hours. The liquid was then evaporated and the remaining polymer was weighed.

$$\% \text{ Protection} = \frac{\text{mg of polymer in blank} - \text{mg of polymer in treated sample}}{\text{mg of polymer in blank}} \times 100$$

Results are shown in Table I.

TABLE I

Heat induced gum test
Ethylenically unsaturated monomer in isoprene

| Treatment | ppm | mg of Polymer | % Protection |
|---|---|---|---|
| Blank | — | 104 | — |
| UOP-5 | 15 | 64 | 38 |
| I-3 | 15 | 65 | 38 |
| Eugenol | 15 | 105 | 0 |
| BHA | 15 | 83 | 20 |
| UOP-5/Eugenol | 15/15 | 0 | 100 |
| UOP-5/BHA | 15/15 | 0 | 100 |
| I-3/BHA | 15/15 | 2 | 98 |

In another set of experiments, the isoprene solution was purged with argon for 10 minutes to remove any air dissolved in the liquid and then pressurized with nitrogen. By purging the liquid with argon, less than 10 ppm of oxygen remained in solution (as measured with an Orbisphere probe), which simulates more closely the conditions in a fractionation tower. The rest of the test was carried out as described above. Results are shown in Table II.

TABLE II

Heat induced gum test.
Ethylenically unsaturated monomer is isoprene.

| Treatment | ppm | Mg. of Gums | % Protection |
|---|---|---|---|
| Blank | — | 71 | — |
| UOP-5 | 10 | 60 | 15 |
| Eugenol | 10 | 94 | None |
| UOP/Eugenol | 10/10 | 3 | 96 |
| I-3/Eugenol | 10/10 | 13 | 81 |

UOP is UOP-5 ®, available from UOP.
I-3 is Naugard I-3, available from Uniroyal.

These results indicate the efficacy of the combination of a methoxyphenol compound and a phenylenediamine compound. These results further indicate that the combination proves more efficacious than either ingredient alone.

While this invention has been described with respect to particular embodiments thereof, it is apparent that numerous other forms and modifications will be obvious to those skilled in the art. The appended claims generally should be construed to cover all such obvious forms and modifications which are within the true spirit and scope of the present invention.

Having thus described the invention, what I claim is:

1. A composition for inhibiting the polymerization of ethylenically unsaturated monomers comprising a methoxyphenol compound selected from the group consisting of eugenol and 2-tert-butyl-4-hydroxyanisole and a phenylenediamine compound.

2. The composition as claimed in claim 1 wherein said phenylenediamine compound is N,N'-bis-di-sec-butyl-p-phenylenediamine.

3. The composition as claimed in claim 1 wherein said phenylenediamine compound is N-phenyl-N'-(1,4-dimethylpentyl)-p-phenylenediamine.

4. The composition as claimed in claim 1 further comprising an organic solvent.

5. The composition as claimed in claim 4 wherein said organic solvent is selected from the group consisting of xylene and heavy aromatic naphtha.

6. A method for inhibiting the polymerization of ethylenically unsaturated monomers comprising adding to said monomers an effective polymerization inhibiting amount of a methoxyphenol compound selected from the group consisting of eugenol and 2-tert-butyl-4-hydroxyanisole and phenylenediamine compound.

7. The method as claimed in claim 6 wherein said phenylenediamine compound is N,N'-bis-di-sec-butyl-p-phenylenediamine.

8. The method as claimed in claim 6 wherein said phenylenediamine compound is N-phenyl-N'-(1,4-dimethylpentyl)-p-phenylenediamine.

9. The method as claimed in claim 6 wherein said methoxyphenol compound and said phenylenediamine compound are added to said ethylenically unsaturated monomer in an amount ranging from about 1 part per million to about 10,000 parts per million parts monomer.

10. The method as claimed in claim 6 wherein said methoxy phenol compound and said phenylenediamine compound are added to said ethylenically unsaturated monomers in a solvent.

11. The method as claimed in claim 10 wherein said solvent is selected from the group consisting of xylene and heavy aromatic naphtha.

12. The method as claimed in claim 6 wherein said ethylenically unsaturated monomer is selected from the group consisting of isoprene and butadiene.

* * * * *